US009700381B2

(12) United States Patent
Amat Girbau

(10) Patent No.: US 9,700,381 B2
(45) Date of Patent: Jul. 11, 2017

(54) MINIMALLY INVASIVE LAPAROSCOPIC SURGICAL PLIERS

(75) Inventor: Josep Amat Girbau, Barcelona (ES)

(73) Assignee: UNIVERSITAT POLITECNICA DE CATALUNYA, Barcelona (ES)

( * ) Notice: Subject to any disclaimer, the term of this patent is extended or adjusted under 35 U.S.C. 154(b) by 306 days.

(21) Appl. No.: 13/504,477

(22) PCT Filed: Oct. 26, 2010

(86) PCT No.: PCT/EP2010/066111
§ 371 (c)(1),
(2), (4) Date: May 4, 2012

(87) PCT Pub. No.: WO2011/051253
PCT Pub. Date: May 5, 2011

(65) Prior Publication Data
US 2012/0209315 A1    Aug. 16, 2012

(30) Foreign Application Priority Data
Oct. 27, 2009    (ES) .................................. 200902132

(51) Int. Cl.
*A61B 34/00* (2016.01)
*A61B 17/29* (2006.01)

(52) U.S. Cl.
CPC .............. *A61B 34/70* (2016.02); *A61B 34/71* (2016.02); *A61B 17/29* (2013.01);
(Continued)

(58) Field of Classification Search
CPC ............ A61B 2019/2242; A61B 19/22; A61B 1/0052; A61B 1/0053; A61B 1/0057;
(Continued)

(56) References Cited

U.S. PATENT DOCUMENTS 6,969,385 B2 * 11/2005 Moreyra ............................ 606/1
7,410,483 B2 * 8/2008 Danitz et al. ..................... 606/1
(Continued)

FOREIGN PATENT DOCUMENTS

| JP | 2001-321385 A | 11/2001 |
|---|---|---|
| JP | 2008-521485 A | 6/2008 |
| WO | 2006057702 A2 | 6/2006 |

OTHER PUBLICATIONS

International Search Report, International Application No. PCT/EP2010/066111, International Filing Date Oct. 26, 2010, Date of Mailing Search Report Aug. 2, 2011, 5 pages.
(Continued)

*Primary Examiner* — Christopher L Templeton
*Assistant Examiner* — Lucas Paez
(74) *Attorney, Agent, or Firm* — Peter B. Scull; Hamilton, DeSanctis & Cha LLP

(57) ABSTRACT

Laparoscopic surgical pliers include jaws mounted on a rotating body and first and second transmissions each including at least one tendon including several cables, and each transmission adapted to transmit movement of the jaws and the rotating body, respectively. The tendons of the first and second transmissions are each respectively formed of several cables arranged so that a cross-section of at least one tendon associated with the first transmission has a variable geometry therealong formed by a first arrangement in which the cables are arranged, in cross-section, with their longitudinal axes in a radial distribution, a second arrangement in which said axes are arranged in a first orientation, and a third arrangement in which said axes are arranged in a second orientation, perpendicular to the first orientation.

12 Claims, 2 Drawing Sheets

(52) U.S. Cl.
CPC ............... *A61B 2017/2903* (2013.01); *A61B 2017/2927* (2013.01); *A61B 2017/2932* (2013.01); *A61B 2017/2939* (2013.01)

(58) Field of Classification Search
CPC .... A61B 2017/2912; A61B 2017/2932; A61B 2017/2902; A61B 2017/2903; A61B 2017/2905; A61B 2017/2913; A61B 2017/2915; A61B 2017/2927; A61B 2017/2929; A61B 2017/2933; A61B 2017/2939; A16B 17/29
USPC ..... 606/1, 130, 205, 207; 74/490.05, 490.06
See application file for complete search history.

(56) References Cited

U.S. PATENT DOCUMENTS

| | | | |
|---|---|---|---|
| 7,608,083 B2* | 10/2009 | Lee | A61B 34/20 606/1 |
| 7,615,066 B2* | 11/2009 | Danitz et al. | 606/205 |
| 7,766,894 B2* | 8/2010 | Weitzner et al. | 604/509 |
| 2004/0138700 A1* | 7/2004 | Cooper et al. | 606/205 |
| 2004/0193146 A1* | 9/2004 | Lee | A61B 17/062 606/1 |
| 2008/0015558 A1* | 1/2008 | Harlan | 606/15 |
| 2009/0054726 A1 | 2/2009 | Sakaguchi et al. | |
| 2009/0062602 A1 | 3/2009 | Rosenberg et al. | |
| 2009/0171374 A1 | 7/2009 | Omori | |
| 2009/0192521 A1 | 7/2009 | Braun | |

OTHER PUBLICATIONS

Written Opinion of the International Searching Authority, International Application. No. PCT/EP2010/066111, International Filing Date Oct. 26, 2010, Date of Mailing Written Opinion Aug. 2, 2011, 5 pages.

\* cited by examiner

MINIMALLY INVASIVE LAPAROSCOPIC SURGICAL PLIERS

CROSS REFERENCES TO RELATED APPLICATIONS

This application is a national stage filing based upon international application no. PCT/EP2010/066111, dated 26 Oct. 2010 and published on 5 May 2011 under international publication no. WO 2011/051253, which claims priority to Spanish P 200902132, dated 27 Oct. 2009. Both references are hereby incorporated by reference as though fully set forth herein.

TECHNICAL FIELD

The present invention finds application in the field of robotic surgery and specifically refers to pliers suitable for minimally invasive robotic laparoscopic surgery.

Pliers hereof include a kinematic arrangement provided with jaws that can be opened and closed and which are mounted on a rotating body. The pliers further include a first transmission adapted to transmit movement of the jaws and a second transmission adapted to transmit movement of the rotating body.

BACKGROUND

Current robotic laparoscopic surgical techniques allow high precision operations to be carried out, providing significant advantages especially in certain complex surgeries, including those in which there is great difficulty in accessing a surgical site. In some implementations, laparoscopic surgical pliers described herein are particularly applicable in such type of robotic laparoscopic surgery that is a minimally invasive technique as it is performed through small incisions in the patient. This technique is widely currently employed, such that in many cases it is used as an alternative to conventional laparoscopic surgery.

In this type of robotic surgery, robotic arm devices are employed actuating pliers capable of holding certain tools and instruments. In addition to the surgical precision achieved by the use of computing associated with these operations, direct contact of the surgeon on the patient can be reduced by such mechanisms, with consequent reduction of infections. Through a small incision, cameras and/or pliers are introduced into the patient to perform various operations with minimal trauma and negligible postoperative pain sequel.

The term pliers as used herein according to the intended use should be understood as a tool designed to be coupled to a robotic arm end. This robotic arm is usually operated remotely by a surgeon skilled in robotic laparoscopic operations and it is designed to grip and even to hold over any useful tool, body or device.

Many types of laparoscopic pliers exist based on their movement and geometry, which aspects depend to a great extent on the type of operation to which the pliers are ultimately intended. In a laparoscopic surgical operation several pliers are typically used, which usually have a configuration such that its distal end is provided with jaws having different configurations as mentioned above, for example, with or without teeth, having a straight or curved shape, etc.

One example of laparoscopic pliers used in robotic laparoscopic surgery is described in U.S. Pat. No. 6,969,385. This document shows pliers used in a robotic device consisting of jaws fitted on a rotating body. The jaws comprise fingers that can be rotated to each other. The transmission of rotational movement of the fingers of the jaws is carried out through cables wound around grooved pulleys. The pulleys are mounted in correspondence with the axes of rotation of the fingers and the shaft of said rotating body that is attached to the robotic arm end, respectively.

A further example of transmission of movement of the pliers is by means of gears. In US2009192521 a surgical instrument is described consisting of pliers including a fixed finger and a movable finger. The moving finger of the pliers is driven through a gear train mechanism.

The use of cables and pulleys or gears in pliers as those described in this document is necessary for transmitting movement from driving means to pliers themselves for positioning them and for moving the jaws. This results in a pliers mechanism that is considerably complex. This mechanical complication is of great importance in the case in which the movement transmission cables have to pass through an articulated body, which usually occurs in the above described pliers. The fact that the transmission cables have to pass through an articulated body requires the provision of additional pulleys for being able to perform such transmission of movement from driving means to jaws.

Laparoscopic surgical pliers are provided having a configuration that allows movement to be transmitted through a kinematic assembly comprising various rotating members, from a driver to rotating members. This kinematic assembly of the pliers comprises members allowing the pliers to be positioned and members allowing jaws of pliers to be moved. As it will be seen hereinafter, the laparoscopic surgical pliers provide a simple, compact and reliable configuration, resulting in additional advantages, as it will be seen in the following.

SUMMARY

Pliers suitable for being used in a robotic arm are provided. More specifically, the pliers are adapted to be used to carry out minimally invasive laparoscopic surgical operations, driven by robotic arms.

Pliers for use in robotic laparoscopic surgical operations are provided including a main body having a proximal end and a distal end. The proximal end of the body is adapted to receive a universal joint capable to perform two passive rotations. At the distal end of the main body a kinematic assembly is coupled formed by a rotating body that is rotatably mounted on that end and being provided with jaws. This rotating body is capable of performing several active rotations.

The jaws of the pliers include at least two moving parts or fingers that can be rotatably driven independently. The movement of the fingers of the pliers is performed by a first transmission. For its part, the rotary movement of the rotating body is carried out through a second transmission. Said first and second transmissions are driven by a driver comprising, for example, electric motors. The combination of the driver and the first and second transmissions allows the pliers to be suitably positioned and allows the jaws to be opened and closed, moving the fingers towards and away from each other.

Both the first and second transmissions include tendons extending inside the main body therealong, between the proximal end and the distal end. In use, said tendons can be moved lengthways along said main body.

More specifically, the pliers comprise at least one tendon associated with the first transmission and one tendon associated with the second transmission. The first transmission may comprise one or two tendons depending on the embodiment of the pliers, either for controlling one or more fingers of the pliers, depending on the application to which the pliers are intended.

Each of said tendons is formed of several steel cables, preferably three, which are arranged packed inside a sheath that encloses them therein. The cables forming each tendon have preferably a circular cross-section to obtain the greater stiffness as possible, and thus avoid buckling when under compression. With this section, friction of tendon with the sheath thereof is also reduced.

The packaging of several cables to form each tendon for transmitting the movement of the pliers provides the necessary stiffness both for being able to work to compression and to traction, allowing efficient power transmission as if it were a rod transmission.

The cross-sectional geometry of each tendon is defined by the arrangement of the cables forming the tendon. The arrangement of cables is such that the tendon, in the vicinity of the distal end of the main body, has a cross-section with variable geometry along its length. This is met at least for tendons associated with the first transmission. Therefore, the variation in the cross-sectional geometry of the tendon allows a very efficient operation of the jaws.

With this configuration, the pliers can be rotated about a first axis and the rotating body can be rotated about a second axis. The first axis and the second axis may be disposed substantially orthogonal to each other.

In one embodiment of the pliers, it is preferred that the variation of the cross-sectional geometry of each tendon is as follows. As stated above, the tendons extend lengthways through the interior of the main body, defining a first cross-sectional geometry arrangement of the tendons in which the respective cables are arranged, in cross-section, with their longitudinal axes in a radial distribution. Then the cross-sectional geometry of the tendons is changed into a second arrangement in which the respective cables are arranged, in cross-section, with their longitudinal axes in a distribution in a first orientation. Finally, the cross-sectional geometry of the tendons is changed into a third arrangement, in which the respective cables are arranged, in cross-section, with their longitudinal axes in a second orientation, different from said first orientation.

In other words, in the first arrangement of the cross-sectional geometry of the tendons, the cables of each tendon in most of the length of the main body are arranged radially, so that the cross-section of the tendon is substantially circular in shape. In other words, if it is a tendon formed of three cables, for example, as noted above, the cables would be arranged, in such a case, with their respective longitudinal axes in a substantially triangular arrangement, in cross section. In one portion corresponding to the vicinity of the distal end of the main body, the cross-section of the same tendon is changed into said second arrangement in which its cables are arranged with their respective longitudinal axes aligned transversely in a first orientation, for example horizontally aligned. The necessary flexibility to overcome the flexion of the joint in the direction parallel to its axis of rotation is therefore obtained. Finally, the cross-section of the tendon is changed into this third arrangement in which the cables are arranged with their respective longitudinal axes transversely aligned in a second orientation, forming an angle to said first orientation, for example 90°, i.e., vertically aligned. In this way the necessary flexibility to overcome the flexion of the joint in the direction perpendicular to the above is therefore obtained.

The first and second transmissions including said tendons further include rotating drums for tangential winding of tendons. These drums allow, in said distal end of the assembly, the longitudinal movement from the tendons to be converted into a rotational movement in two directions, i.e., both to traction and to compression, to rotatably drive the rotating body of the pliers and their jaws. Said drums have a grooved periphery suitable for winding of the tendons. The rotating body of the pliers is formed by two of said drums, which are arranged overlapped. Each of said two drums for winding of the rotating body is integral with each jaw finger, respectively.

The change in the cross-section configuration of tendons (at least that of those associated with the first transmission means), as it moves along its length toward the distal end of the main body, allows an effective winding and twisting of the tendon in respective drums in both directions of travel.

In order to cause the cross-sectional geometry of each tendon to be changed, as indicated, at different planes in the vicinity of the distal end of the main body, several tendon changing orientation modules are provided. Each changing orientation module includes a block fixed to the interior of the elongated body within which elongated channels are formed that are shaped to guide the cables of each tendon in one rotation (e.g. at 90°).

Two changing orientation modules are used for each tendon, which makes it possible the above mentioned two changes in the tendon cross-sectional shape (from circular to straight in a first orientation, and from straight in said first orientation to straight in a second, different orientation). Each changing orientation module may have a first dimension (width or height) corresponding, for example, to a diameter of a cable used and a second dimension (width or height) corresponding, for example, to three of said diameters. Between two changing orientation modules in the same tendon length, the cables thereof are housed inside a flat sheath suitable to maintain the configuration thereof.

For the transmission of movement through the displacement of the tendons along the elongated body driving means are used, as stated above, such as electric motors. In one embodiment, other means may be adapted to rotatably drive internally threaded tubes which are mounted axially retained within the main body. Inside such internally threaded tubes a corresponding externally threaded tube is received that is fixed to the outer sheath within which tendon cables are disposed. The externally threaded tube can be rotated to said internally threaded tube (retained axially within the main body) so that the rotation thereof through the driver results in a longitudinal movement of the outer threaded tube and consequently, a longitudinal movement of the tendon of the first transmission (to drive the fingers from the pliers jaws) or the second transmission (for rotatably driving the moving body for positioning the jaws).

With the pliers as described, an assembly having a great mechanical simplification over the pliers which for the same purpose have been used so far, with consequent cost savings. With the variable geometry cross-section configuration of the tendons of the driving means of the pliers for each change of orientation of said section it is possible to dispense with the use of idler pulleys or gears for transverse rotation of parts where the tendons run. The configuration further allows a very robust assembly to be obtained with a large durability of the cables as well as the drums around which they are to be rolled up.

Other objects, advantages and features of the minimally invasive laparoscopic surgical pliers hereof will become apparent from the description of a preferred embodiment hereof. This description is given only by way of an example and it is shown in the accompanying drawings.

BRIEF DESCRIPTION OF DRAWINGS

In said drawings.

DETAILED DESCRIPTION OF A PREFERRED EMBODIMENT

Figure 1:
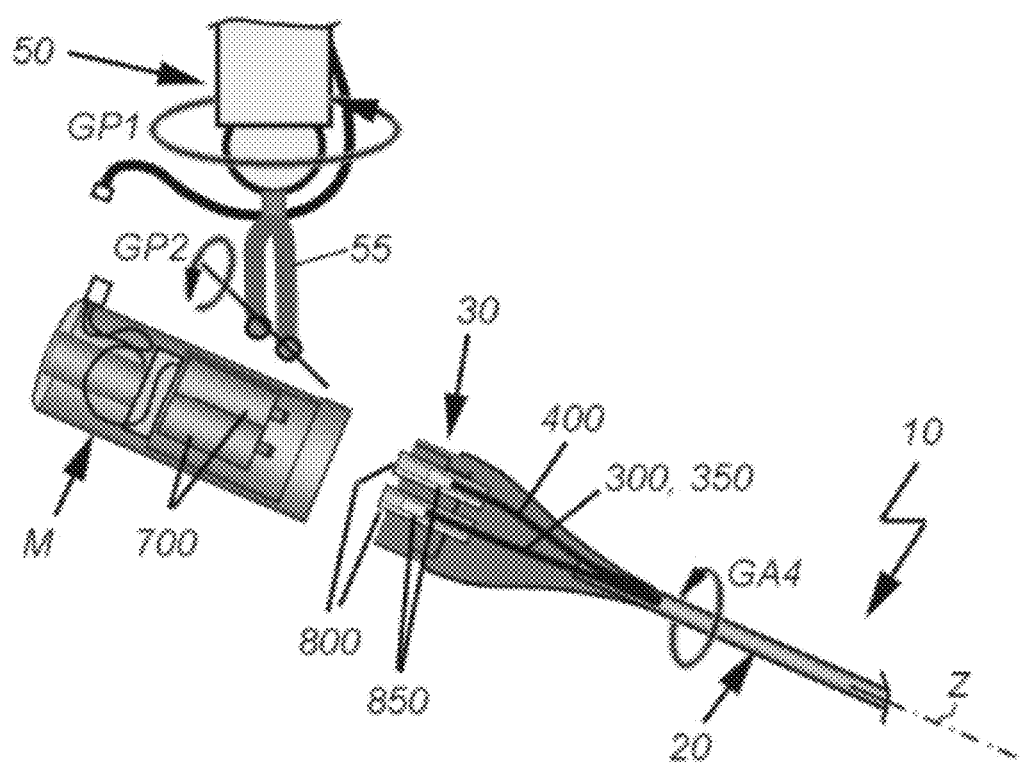
FIG. 1 is a perspective part view of a main body of the minimally invasive laparoscopic surgical pliers.

In the FIGS. 1-4 enclosed herein a preferred embodiment of minimally invasive laparoscopic surgical pliers in robotic arms is shown. Pliers have been indicated in the figures as a whole by reference numeral 10.

Pliers 10 include, in the exemplary embodiment shown, an elongated shaped main body 20 having a proximal end 30 (left-hand side in the figures) and a distal end 40 (right-hand side in the figures). The main body 20 of the pliers 10 with its proximal end 30 is partly shown in the FIG. 1 of the drawings. The distal end 40 of the main body 20 is shown in the FIGS. 3 and 4 of the drawings.

As shown in FIG. 1, the proximal end 30 of the body 20 of the pliers 10 can be attached to a robotic arm 50 through a universal joint 55. For the sake of clarity, the universal joint 55 is shown in said FIG. 1 separated from the main body 20. The universal joint 55 allows the assembly to perform two passive rotations GP1, GP2, as shown in FIG. 1 by respective arrows. At the distal end 40 of the body 20 a kinematic assembly is coupled comprising a body 60 pivotally mounted on the distal end 40. The rotating body 60 is provided with jaws 70, which will be described in greater detail hereinafter.

Figure 3:
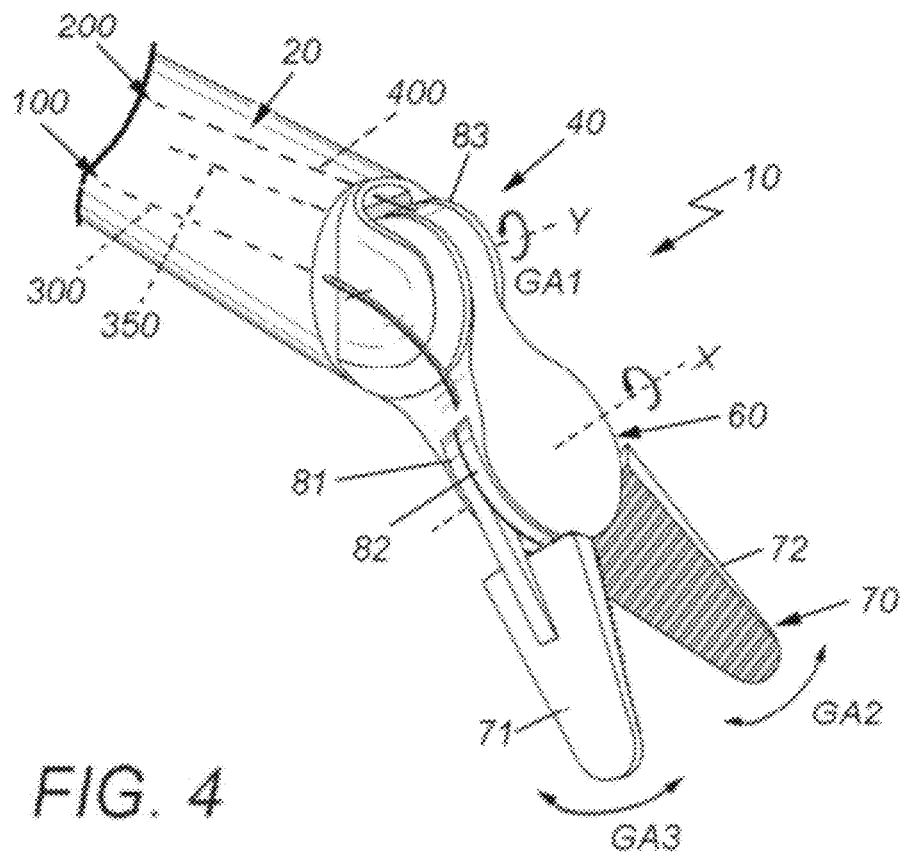
FIG. 3 is a perspective part view of the minimally invasive laparoscopic surgical pliers, with jaws and a rotating body mounted at a distal end in the main body of an assembly.
Figure 4:
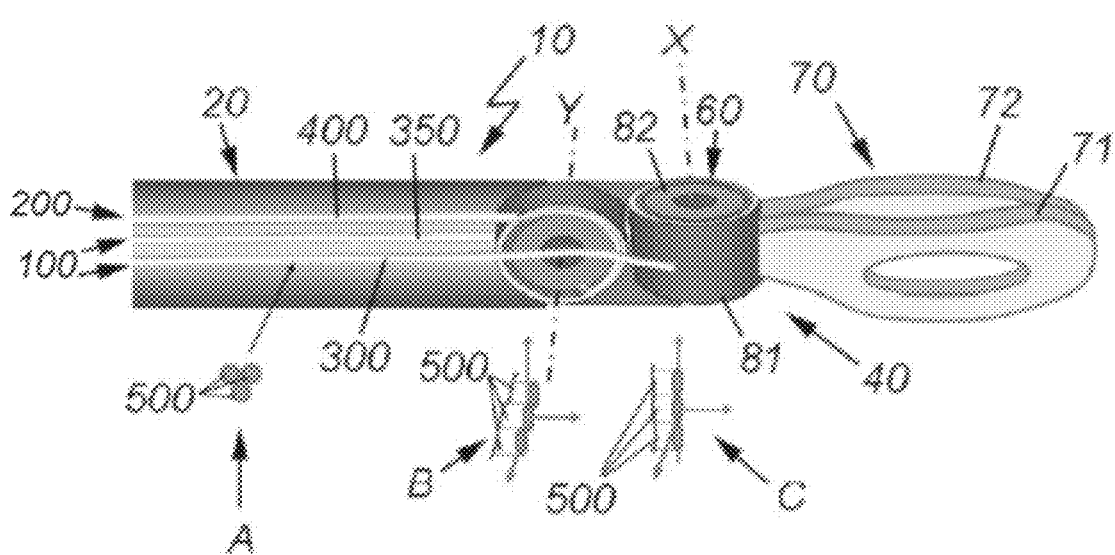
FIG. 4 is a perspective part view of the pliers in which the configuration of the tendons and the change of orientation thereof are diagrammatically shown.

The jaws 70 of the embodiment illustrated by way of an example in FIGS. 3 and 4 include two scoop-shaped fingers 71, 72. In the embodiment of FIG. 3, the fingers 71, 72 of the jaws 70 have a flat, rough inner surface. In the embodiment of FIG. 4, the fingers 71, 72 of the jaws 70 have a curved, smooth inner surface. It will be understood, however, that fingers 71, 72 of pliers 70 may have any other configuration as well as an inner surface having different surface finishes as required.

The fingers 71, 72 of the jaws 70 may be rotatably driven in a coordinated and independent way according to active rotating movements GA2, GA3 shown in FIG. 3, about a first axis X, for moving towards and/or away to each other. This allows the pliers 10 to grip and even to hold over any useful tool, body or device (not shown).

The kinematic assembly of the pliers 10 can also be rotated around the longitudinal axis Z of the main body 20 according to the passive angular movement GA4 depicted in FIG. 1. This passive rotation GA4 is performed at an angle greater than 360° and allows positioning of the working plane of the pliers 10.

Each finger 71, 72 of the jaws 70 is integral with a winding drum 81, 82 respectively, which will be described in detail further on.

At the proximal end 30 of main body 20 a driver M is provided for controlled driving of jaws 70 and its orientation in the space. The driver M will be described in greater detail further below.

In collaboration with the driver M, a first movement transmission mechanism (or as referred to herein as a first transmission 100) are provided for causing the fingers 71, 72 of the jaws 70 to be rotated towards and away from each other, as depicted in FIG. 3 by GA2 and GA3 for each finger 71, 72, respectively. A second movement transmission mechanism (referred to as a second transmission 200) are also provided for causing the rotating body 60 to be rotated according to GA1 around a second axis Y, as shown in FIG. 3, for positioning the pliers 10 sideways in the space when used in a laparoscopic intervention. In one embodiment it is preferred the first axis X and the second axis Y form an angle of 90° to each other.

The first transmission 100 includes tendons 300, 350, and the second transmission includes one tendon 400, respectively. Tendon 350 is arranged symmetrically with respect to tendon 300 and it is therefore hidden in FIG. 3 of the drawings (shown in dashed lines). It is clear that in other embodiments, the pliers 70 could include a single mobile finger, the other one being fixed, so that the first transmission 100 would include, in this case, a single tendon (300 or 350).

Tendons 300, 350, 400 all extend along the main body 20, from proximal end 30 to distal end 40, as it can be seen in FIGS. 3 and 4 of the drawings. Tendons 300, 350, 400 are adapted to be moved lengthways within the main body 20 therealong to drive the pliers 10, as will be described in detail below.

In the embodiment shown by way of example, tendons 300, 350, 400 of transmissions 100, 200 are each formed by three steel cables 500 having a circular cross-section arranged packaged within a sheath that encloses them (not shown) providing the necessary rigidity for working both to traction and to compression.

Figure 2:
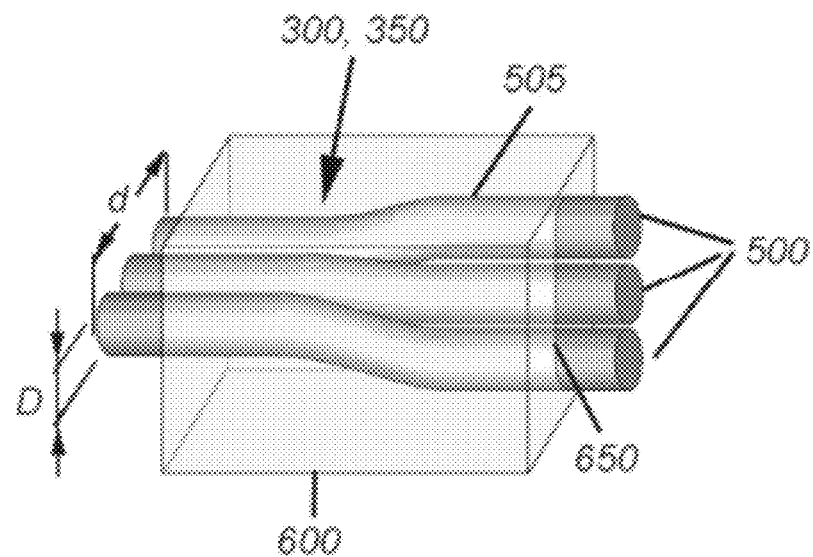
FIG. 2 is a perspective view of one embodiment of one module for changing an orientation in a tendon of the pliers.

Several arrangements of the cables 500 in one tendon 300, 350, 400 are shown in FIGS. 2 and 4. FIG. 4 shows the various arrangements A, B, C of the cross-sectional geometries taken on by at least tendons 300, 350 associated with the first transmission 100. This variation in the cross-sectional geometry of tendons 300, 350 is defined by the arrangement or orientation of cables 500 forming each tendon. In the embodiment shown, the arrangement of cables 500 in tendons 300, 350 is such that, near the distal end 40 of the main body 20, tendons have their cross-sectional geometry changed as they advance lengthways towards the distal end 40 of main body 20 of the pliers 10. This variation in the cross-sectional geometry of tendon 300, 350 allows the rotational movement GA2, GA3 of the fingers 71, 72 of the jaws 70 around axis X in both directions and allows tendons 300, 350 associated with the first transmission 100 to be passed through the joint of the rotating body 60, as it will be described below.

The variation in the cross-sectional geometry of each tendon 300, 400 will be described below with reference to FIG. 4 of the drawings. The cross-sectional geometry of each tendon 300, 350 is changed twice on its path, so there is a first cross-sectional geometry arrangement A of tendon 300, 350, a second cross-sectional geometry arrangement B of tendon 300, 350, and a third cross-sectional geometry arrangement C of tendon 300, 350. Arrangements A, B and C are schematically shown in FIG. 4.

According to FIG. 4, in most of the length of the main body 20 tendons 300, 350 run with their respective cables 500 arranged radially from the proximal end 30 to the distal end 40. This radial arrangement of the cables 500 is achieved by a substantially triangular arrangement thereof, as seen in cross-section, defining a substantially circular shape for the first cross-sectional geometry arrangement A of tendon 300, 350. Near the distal end 40 of the main body 20, the cross-sectional geometry of the same tendon 300, 350 is changed from a first arrangement of cables 500 (radially) with their longitudinal axes triangularly distributed into a second arrangement B with their longitudinal axes aligned in a first orientation, horizontally aligned, as seen in cross-section such as shown in FIG. 4. Finally, the cross-sectional geometry of tendon 300, 350 is changed again from this second arrangement B of the cables 500 (in the first orientation, with their longitudinal axes aligned horizontally) into an arrangement in which said longitudinal axes are aligned in a second orientation, thus defining a third arrangement C of the cross-sectional geometry of tendon 300, 350, as shown in FIG. 4. For the disclosed embodiment, the first orientation in the second arrangement B of the cross-section of tendon 300, 350 forms an angle of substantially 90° to the second orientation of the third arrangement C of the cross-section of the tendon 300, 350. Therefore, the third arrangement C of the cross-section of tendon 300, 350 corresponds to one in which its cables 500 are arranged vertically aligned, as seen in cross-section, as shown seen in FIG. 4.

The cross-section of tendons 300, 350 of pliers 10 provides the rigidity needed for working to traction and to compression, and at the same time it allows tendons to be wound around each drum 81, 82, 83 accordingly. The change in orientation of at least tendons 300, 350 in the first transmission 100 (not needed for tendon 400 associated with the second transmission 200 in the embodiment shown) further allows the passage of the tendons 300, through joint 350 associated with axis Y, to be adapted, i.e., that allowing rotation of the body 60 according to rotation GA1.

As mentioned above, the first and second movement transmissions 100, 200 formed by the respective tendons 300, 350, 400 further include rotating drums 81, 82, 83 around which the above mentioned corresponding tendons 300, 350, 400 are wound. In particular, drums 81, 82 are arranged coaxially one above the other forming the rotating body 60 of the pliers 10 and they are adapted to be rotatably driven independently by actuation of the first transmission 100, that is by tendon 300, and tendon 350 (symmetric thereto, not visible) respectively. Tendon 300, which extends along the interior of the main body 20, surrounds the periphery of drum 81, while tendon 350, which extends along the interior of the main body 20, surrounds the periphery of drum 82. Finally, tendon 400, which also extends along the interior of the main body 20, surrounds the periphery of drum 83. Displacement of tendons 300, 350 associated with the first transmission 100 causes respective independent rotation of respective drums 81, 82 of the rotating body 60 of pliers 10, causing the fingers 71, 27 of the jaws 70 to be rotated independently around axis X according to the respective active rotating movements GA2, GA3 depicted in FIG. 3, rotating around axis X towards or away from each other, as desired, to grip, hold over, etc. instruments, organs, etc. Displacement of tendon 400 associated with the second transmission 200 causes rotation of the drum 83 making the rotating body 60 of the pliers 10 to be rotated around axis Y according to active movement GA1 shown in FIG. 3, for proper positioning of pliers 10 in the space.

For a proper rotating movement of drums 81, 82, 83, they are provided with a grooved periphery (not shown) suitable for winding of the respective tendons 300, 350, 400. Each winding drum 81, 82 defining the rotating body 60 is integral with each respective finger 71, 72 of the jaws 70.

In the embodiment of the minimally invasive laparoscopic surgical pliers 10 that is described herein according to the figures, a module 600 for changing orientation of tendons 300, 350 is further provided. One example of one of these changing orientation modules 600 is shown in FIG. 2. In said FIG. 2 a module 600 for changing orientation of tendons 300, 350 is shown designed for causing a change in the cross-sectional geometry arrangement A, B, C of each tendon 300, 350 in said first transmission 100 at different planes in the vicinity of the distal end 40 of the main body 20 of pliers 10. The changing orientation module 600 includes an integrated block fixed inside the main body 20. Inside the changing orientation module 600 an elongated inner channel 650 is provided shaped to guide the cables 500 of each tendon 300, 350 and to force them to be rotated about 90° as they are passed through the interior of the channel 650.

For each tendon 300, 350 of the first transmission 100 two changing orientation modules 600 are provided. Modules 600 associated with said first movement transmission 100, i.e., those causing the change in orientation of tendons 300 and 350 when moving lengthways around the main body 20, are arranged one just at the distal end 40 of the main body 20 and the other one in the vicinity of each of the respective drums 81, 82 of the rotating body 60.

The configuration described for changing orientation modules 600 allows two changes in the cross-sectional arrangement of the tendons, from circular A to straight horizontal B, and from straight horizontal B finally to straight vertical C, as diagrammatically shown in FIG. 4 and such as described above.

The inner channel 650 of each changing orientation module 600 may have a first dimension d corresponding to the diameter of cable used (typically 0.3 mm) and a second dimension D corresponding to three of said diameters (0.9 mm). It will be understood that said dimensions d, D in a particular orientation may correspond to width and height of said channel 650 in the example shown, although the geometry of the module 600 can be defined by other dimensions.

Between two changing orientation modules 600 in the same tendon 300, 350, cables 500 are housed inside a flat sheath suitable to maintain their configuration in that path between two modules 600.

Turning now to FIG. 1 of the drawings, driver M for displaceably driving the tendons 300, 350, 400 are described below in greater detail.

In the embodiment illustrated by way of an example, driver M may include several electric motors 700 adapted for rotatably driving outer tubes 800. These outer tubes 800 are provided with an inner thread and they are axially retained in the proximal end 30, inside the main body 20, as shown in FIG. 1. Inside the outer tubes 800 corresponding inner tubes are threadably received having an outer thread 850, attached to the exterior of respective tendons 300, 350, 400. The inner tubes 850 can be rotated relative to the respective outer tubes 800 which, as noted above, are axially retained within the main body 20. Thus, rotation of each outer tube 800 through the corresponding motor 700 results in longitudinal movement of the inner tube 850 and, consequently, in a corresponding longitudinal movement of the tendon 300, 350 of the first transmission 100 for actuating the fingers 71, 72 of the jaws 70 of the pliers 10 around axis X (independent movements GA2, GA3), and/or of the second transmission 200, for rotatably driving the movable body 60 for positioning the jaws 70 around the axis Y (movement GA1).

While the present developments have been described in the specification and illustrated in the accompanying drawings with reference to a preferred embodiment thereof, the minimally invasive laparoscopic surgical pliers are susceptible to various changes without departing from the scope of protection defined in the appended claims.

The invention claimed is:

1. Minimally invasive laparoscopic surgical pliers comprising: jaws mounted on a rotating body, a first transmission having at least one tendon adapted to transmit movement of the jaws and a second transmission having at least one tendon adapted to transmit movement of the rotating body,
wherein said tendons of said first and second transmissions are each respectively formed by several cables distributed defining a cross-sectional geometry of each tendon, the cross-sectional geometry thereof defined as the intersection of each tendon in three-dimensional space with a plane that cuts each tendon transversely, at right angles to the longest axis of each tendon, the cables being distributed such that their positioning can be varied within the tendon along its path through an interior of a main body resulting in a corresponding variation in the cross-sectional geometry of the tendon;
wherein the pliers further comprise modules for changing distribution of the cables in each tendon, each module being formed by a block within which an elongated channel is formed and shaped to guide said cables of the corresponding tendon causing a rotation on its distribution; and
wherein the cross sectional geometry of the tendon in at least the first transmission has at least first, second and third parts thereof disposed along the main body of the same tendon having at least three different cross-sectional geometries defined according to corresponding different distributions of the cables in each tendon at the first, second and third parts thereof:
a first part cross-sectional geometry of the tendon in which the respective cables are distributed radially in the tendon cross-section, with their respective longitudinal axes arranged in a radial distribution;
a second part cross-sectional geometry of the tendon in which the respective cables are distributed in the tendon cross-section with their respective longitudinal axes arranged according to a first distribution, with their respective longitudinal axes aligned; and
a third part cross-sectional geometry of the tendon in which the respective cables are distributed in the tendon cross-section with their respective longitudinal axes arranged according to a second distribution, different from the first distribution, with their longitudinal axes forming an angle to said first distribution.

2. The pliers as recited in claim 1, wherein said first and second cable distributions, in the second and third cross-sectional geometries of the tendons, respectively, form an angle of substantially 90° to each other.

3. The pliers as recited in claim 1, wherein at least one of said tendons is formed by at least three cables.

4. The pliers as recited in claim 3, wherein in the first cross-sectional geometry of the tendon the cables are distributed in a substantially triangular arrangement; in the second cross-sectional geometry of the tendon the cables are distributed with their longitudinal axes horizontally aligned; and in the third cross-sectional geometry of the tendon the cables are distributed with their longitudinal axes vertically aligned.

5. The pliers as recited in claim 1, wherein the jaws are adapted to be rotated about a first axis.

6. The pliers as recited in claim 1, wherein said rotating body can be rotated about a second axis.

7. The pliers as recited in claim 1 wherein the jaws are adapted to be rotated about a first axis and the rotating body is adapted to be rotated about a second axis, said first and second axes forming an angle of substantially 90° to each other.

8. The pliers as recited in claim 1, wherein said rotating body comprises rotating drums that are respectively associated with said jaws.

9. The pliers as recited in claim 8, wherein said rotating drums are adapted to be operated independently each by a respective tendon of said first transmission.

10. The pliers as recited in claim 8, wherein the rotating drums are configured for tangential winding of tendons.

11. The pliers as recited in claim 8, wherein the rotating drums are configured so that longitudinal movement from the tendons is converted into a rotational movement in two different directions to rotatably drive the rotating body of the jaws.

12. The pliers as recited in claim 1, wherein the pliers further include at least one sheath enclosing the tendons therein.

* * * * *